US012629402B2

(12) United States Patent
Dal Monte et al.

(10) Patent No.: US 12,629,402 B2
(45) Date of Patent: May 19, 2026

(54) PREPARATION OF INSOLUBLE POLYSACCHARIDES OBTAINED FROM PLANT CELL CULTURES IN SUSPENSION FOR THE TREATMENT OF CLOSTRIDIUM DIFFICILE INFECTIONS

(71) Applicant: ABRESEARCH SRL, Brendola (IT)

(72) Inventors: Renzo Dal Monte, Brendola (IT); Andrea Carpi, Brendola (IT); Ignazio Castagliuolo, Brendola (IT); Paola Brun, Brendola (IT)

(73) Assignee: ABRESEARCH SRL, Brendola (IT)

( * ) Notice: Subject to any disclaimer, the term of this patent is extended or adjusted under 35 U.S.C. 154(b) by 960 days.

(21) Appl. No.: 17/611,114

(22) PCT Filed: May 14, 2020

(86) PCT No.: PCT/IB2020/054580
§ 371 (c)(1),
(2) Date: Nov. 12, 2021

(87) PCT Pub. No.: WO2020/230080
PCT Pub. Date: Nov. 19, 2020

(65) Prior Publication Data
US 2022/0241361 A1      Aug. 4, 2022

(30) Foreign Application Priority Data

May 15, 2019      (IT) ........................ 102019000006858

(51) Int. Cl.
| | |
|---|---|
| *A61K 36/28* | (2006.01) |
| *A61K 36/31* | (2006.01) |
| *A61K 36/34* | (2006.01) |
| *A61K 36/484* | (2006.01) |
| *A61K 36/68* | (2006.01) |
| *A61P 31/04* | (2006.01) |
| *C07K 14/33* | (2006.01) |

(52) U.S. Cl.
CPC .............. *A61K 36/28* (2013.01); *A61K 36/31* (2013.01); *A61K 36/34* (2013.01); *A61K 36/484* (2013.01); *A61K 36/68* (2013.01); *A61P 31/04* (2018.01); *C07K 14/33* (2013.01)

(58) Field of Classification Search
None
See application file for complete search history.

(56) References Cited

U.S. PATENT DOCUMENTS

| | | | |
|---|---|---|---|
| 2007/0249524 A1 | 10/2007 | Dieckgraefe | |
| 2017/0000834 A1 | 1/2017 | Klosterbuer et al. | |

FOREIGN PATENT DOCUMENTS

| | | | |
|---|---|---|---|
| EP | 2222310 B1 | 8/2016 | |
| KR | 20120122664 B1 | 12/2013 | |
| WO | 2004/061090 A1 | 7/2004 | |

OTHER PUBLICATIONS

Bernabe (Microbial Research (2024), vol. 286, No. 127812, 12 pages).*
International Search Report, issued in PCT/IB2020/054580, mailed Jul. 16, 2020, Rijswijk, NL.
Jun H. I. et al., Characterization of the pectic polysaccharides from pumpkin peel, LWT—Food Science and Technology, Jun. 1, 2006, pp. 554-561, vol. 39, Issue 5, Academic Press, GB.
Sharma M. et al., Echinacea Extracts Contain Significant and Selective Activities Against Human Pathogenic Bacteria, Pharmaceutical Biology, published online Oct. 7, 2008, pp. 111-116, vol. 46, No. 1-2, Informa Healthcare USA Inc.
Smits W. K. et al., Clostridium difficile infection, Nature Reviews—Disease Primers, Apr. 7, 2016, pp. 1-20, Article 16020, vol. 2, MacMillan Publishers Limited, US.
International Written Opinion, issued in PCT/IB2020/054580, mailed Jul. 16, 2020.

* cited by examiner

*Primary Examiner* — Susan Hoffman
(74) *Attorney, Agent, or Firm* — Ferguson Case Orr Paterson

(57) ABSTRACT

An insoluble cell fraction obtained from plant cells cultured in a suspension composed entirely of natural molecules for the treatment of primary and recurrent *Clostridium difficile* infections is provided. A process for the preparation of the insoluble cell fraction is also provided.

20 Claims, 6 Drawing Sheets vehicle      *C. difficile* toxins

*C. difficile*+ toxins

ABR119 100 μg/mL      ABR119 10 μg/mL      ABR119 1μg/mL

*C. difficile*+ toxins
ABR119 100μg/mL
with acid treatment vehicle ABR119 ABR119
with acid treatment vehicle ABR119 ABR119
with acid treatment

PREPARATION OF INSOLUBLE POLYSACCHARIDES OBTAINED FROM PLANT CELL CULTURES IN SUSPENSION FOR THE TREATMENT OF CLOSTRIDIUM DIFFICILE INFECTIONS

CROSS-REFERENCE TO RELATED APPLICATIONS

This application is a National Phase Application of PCT International Application No. PCT/IB2020/054580, having an International Filing Date of May 14, 2020 which claims the benefit of priority to Italian Patent Application No. 102019000006858, filed May 15, 2019, each of which is hereby incorporated by reference in its entirety.

TECHNICAL FIELD OF THE INVENTION

The present invention finds use in the medical field and in particular in the prevention and treatment of both primary and recurrent *Clostridium difficile* infections.

BACKGROUND ART

*Clostridium difficile* is an opportunistic pathogenic Gram-positive spore-forming bacterium.

*C. difficile* is the infectious agent responsible for the largest number of cases of diarrhea and post-antibiotic colitis contracted in hospitals or nursing homes.

It is estimated that in the United States *C. difficile* infections are responsible for more than 14,000 deaths per year with about 5 billion dollars in additional costs to the health-care system.

In the healthy adult population the frequency of colonization by *C. difficile* is less than 10%; however, the pathogen mainly spreads in nosocomial structures (hospitals, nursing homes, assisted-living residences) in the form of spores and as such is typically acquired from the environment.

In order to establish an infection, the spores must germinate to give rise to the growth of vegetative bacterial forms, events which occur in the presence of a suitable intestinal environment characterized by an alteration of the intestinal microbiota (dysbiosis).

The main cause of this condition is the patient's intake of antibiotics, which cause the loss of protective bacteria normally present in the digestive tract.

In fact, the incidence of *C. difficile* infection in the United States in 2011 was 12.7% of patients discharged from a hospital.

Due to the absence of competition from normal intestinal microbial flora, *C. difficile* proliferates and produces two potent exotoxins, toxin A and toxin B.

These exotoxins are responsible for damage to the colic mucosa and the resulting clinical manifestations.

To exert their pathogenic action, the toxins must bind to a receptor expressed by intestinal epithelial cells, be internalized, and modify specific intracellular targets.

The toxins transfer a glucose molecule to the Rho enzyme, causing the depolymerization of actin filaments with the loss of function of the tight junctions between epithelial cells, resulting in increased intestinal permeability.

In addition, the epithelial cells release cytokines and chemokines capable of recruiting inflammatory cells from the circulatory stream, leading to the development of a severe inflammatory reaction capable of involving the entire thickness of the mucosa.

The inflammatory process is greatly amplified by the direct action of toxins A and B, which, by exploiting the increased mucosal permeability, are able to reach and activate the inflammatory cells present in the mucosa.

The inflammatory process triggered by *C. difficile* toxins A and B leads to the formation of a massive infiltration rich in neutrophils, which destroys the integrity of the mucosal membrane.

The severity of clinical manifestations of *C. difficile* infection ranges from mild/moderate forms with diarrhea without systemic signs to forms of severe colitis, which can result in toxic megacolon with the impairment of the patient's general conditions, which can cause death.

Treatment depends on the severity of symptoms.

In the mildest forms, it may be sufficient to suspend the antibiotic therapy which caused the development of the infection; however, this is not always possible because the primary infection would remain untreated.

Generally, even in the mildest forms, therefore, *C. difficile* infection requires specific antibiotic therapy (metronidazole or vancomycin), while the more severe forms (toxic megacolon) may require an emergency colectomy.

Although almost all patients with *C. difficile*-induced diarrhea respond positively to antibiotic therapy with symptom resolution, regardless of the antibiotic therapy undertaken, 24-27% of patients will experience relapses.

The onset of relapses is attributable to the relatively long amount of time needed to restore a balanced intestinal microbiota able to counteract the colonization and growth of *C. difficile*; therefore, the production of toxins A and B resumes upon the suspension of antibiotic treatment and, hence, the recurrence of inflammation and diarrheal symptoms.

To date, effective therapies are not available to treat or reduce the incidence of relapses; in fact, although the administration of antibiotics (metronidazole or vancomycin or fidaxomicin) solves the acute problem, it aggravates intestinal dysbiosis, favoring further subsequent relapses.

Among probiotics, *S. boulardii* alone appears to reduce the incidence of relapses but only in combination with antibiotic therapy.

More recently, monoclonal antibody therapies have been introduced to neutralize the toxins and promote microbiota reconstitution, which would physiologically hinder the growth of *C. difficile*; however, this approach is burdened with significant side effects, is very expensive and only applicable to patients who are already experiencing recurrence.

Finally, the last approach introduced in clinics is fecal transplantation; however, it is an invasive procedure which is very expensive and risky for the patient.

Fecal transplantation is currently used in a limited number of cases, practically only in subjects who have not responded to previous therapies.

*Clostridium difficile* Toxin Binding and Inactivation Systems

Over the last twenty years, *Clostridium difficile* infections which show resistance to antibiotic treatment and a strong propensity for recurrence with poor prognosis are continuously increasing and spreading, also in non-hospital settings.

For this reason, numerous therapeutic strategies aimed at the prevention and treatment of *Clostridium difficile* infections have been applied and are being developed.

Some of these strategies aim at inactivating the bacterial toxins, which are responsible for the virulence of the bacterium itself, favoring its pathogenicity and the recurrence of infections.

The toxins also cause damage to the intestinal tract, as well as the actual intoxication of the patient.

Some developing approaches target the production of particular synthetic combinations of carbohydrates arranged in small oligosaccharides with the ability to specifically bind the toxins of Clostridium difficile, as proposed for example in US patent application 2007/0249524A1.

In other studies, the use of proteins belonging to the modified mucin family is provided, so as to acquire the ability to stably bind the Clostridium difficile toxins.

In any case, the animal trial has not produced results such as to start clinical trials and in some cases the synthetic or modified molecules could even be immunogenic, inflammatory, or allergenic.

Another system designed for binding the toxins is based on the preparation of soluble anionic compounds based on polystyrene; these therapies, such as Tolevamer© (Genzyme) administered in high doses to patients (6 grams a day) do not show significant advantages over appropriate antibiotic therapy and still have a high risk of inducing alterations in the plasma ionic balance, particular by altering the physiological level of the potassium ion.

An alternative strategy to the above involves the development of monoclonal antibodies capable of selectively binding and inactivating the toxins produced by Clostridium difficile, such as Actoxumab or Bezlotoxumab.

In particular, Bezlotoxumab (Zinplava© developed by Medarex and Massachussetts Biologic Laboratories, Bristol-Myers Squibb and Merck & Co.) was placed on the market at the end of 2016.

The antibody is injected intravenously and is used for the treatment of the most serious Clostridium difficile infections and for the prevention of relapses; however, this therapeutic intervention is accompanied by serious toxic effects on patients including the appearance of cardiomyopathies; its use therefore requires a careful evaluation of the patients which can be treated or are to be treated and the management of the side effects caused by the therapy itself.

Patent document EP 2.222.310 B1 describes the effect on intestinal flora of a product comprising pulp prepared from cranberry and galacto-oligosaccharides, thanks to the microbiota growth regulation mechanism favored, by a competitive mechanism, over harmful bacteria.

US patent document 2017/0000834 A1 describes a preparation comprising fructo-oligosaccharides (FOS) and insoluble fibers which promote the development of the microbiota with respect to Clostridium difficile.

Jun H. I. et al. ("Characterization of pectic polysaccharides from pumpkin peel", 2006) describes a preparation of insoluble polysaccharides which promotes lactobacilli growth in vitro with respect to Clostridium difficile.

Patent document WO 2004/061090 describes an insoluble preparation of polysaccharides, including xylose, arabinose, and glucose, obtained from the distillation of barley, which is soluble in an organic solvent and exhibits cytotoxic activity.

Korean patent document KR 2012 0122664 describes a product extracted in the organic phase from Angelica keiskei, which has an effect on fat and body weight reduction.

Sharma M. et al. ("Echinacea extracts contain significant and selective activities against human pathogenic bacteria", 2007) describes the antibacterial activity of soluble extracts comprising antibacterial molecules, such as caffeic acid and alkylamides. These extracts have an inhibitory effect on the growth of Clostridium difficile, but nothing is reported on the activity against the bacterial toxin.

SUMMARY OF THE INVENTION

The present invention is based on surprisingly having found that an insoluble fraction obtained from plant cells cultured in suspension as capable of binding the toxins produced by Clostridium difficile with high affinity and of inactivating them.

In particular, this insoluble cell fraction has been found to be enriched with natural insoluble polysaccharides.

The inventors of the present patent application have found that the biotechnological platform for the culture of plant cells in suspension allows to obtain a particular insoluble cell fraction capable of binding the toxins produced by Clostridium difficile with high affinity and inactivating them.

Furthermore, this cell fraction is completely composed of complex natural plant molecules.

OBJECT OF THE INVENTION

A first object of the present invention is represented by the medical use of an insoluble cell fraction from plant cells cultured in suspension.

According to particular aspects, the particular insoluble cell fraction of plant cells cultured in suspension finds application for the medical use in the prevention and treatment of primary and/or recurrent Clostridium difficile infections.

In a second object, the invention describes a biotechnological platform for the preparation of an insoluble cell fraction of plant cells cultured in suspension.

According to an additional aspect of the invention, it is described herein a biotechnological process for the preparation of an insoluble cell fraction of plant cells cultured in suspension composed entirely of natural molecules.

The insoluble fraction obtained from the plant cells cultured in suspension obtained according to the process of the invention is a further object of the invention.

According to another aspect, there are described pharmaceutical and/or nutraceutical preparations comprising the insoluble cell fraction obtained from plant cells cultured in suspension.

In another object, the present invention describes a method for the prevention and/or treatment of Clostridium difficile infections comprising the use of an insoluble cell fraction obtained from plant cells cultured in suspension.

In a further object of the present invention, there is described the use of an insoluble cell fraction obtained from plant cells cultured in suspension for binding and inactivating the toxins produced by Clostridium difficile.

In a still further object of the present invention, there is described the use of an insoluble cell fraction obtained from plant cells cultured in suspension for the preparation of a medicine for the prevention and treatment of primary and/or recurrent Clostridium difficile infections.

According to a particular aspect, said medicament for the prevention and treatment of primary and/or recurrent Clostridium difficile infections inactivates Clostridium difficile toxin A and B.

DETAILED DESCRIPTION OF THE INVENTION

Figure 1:
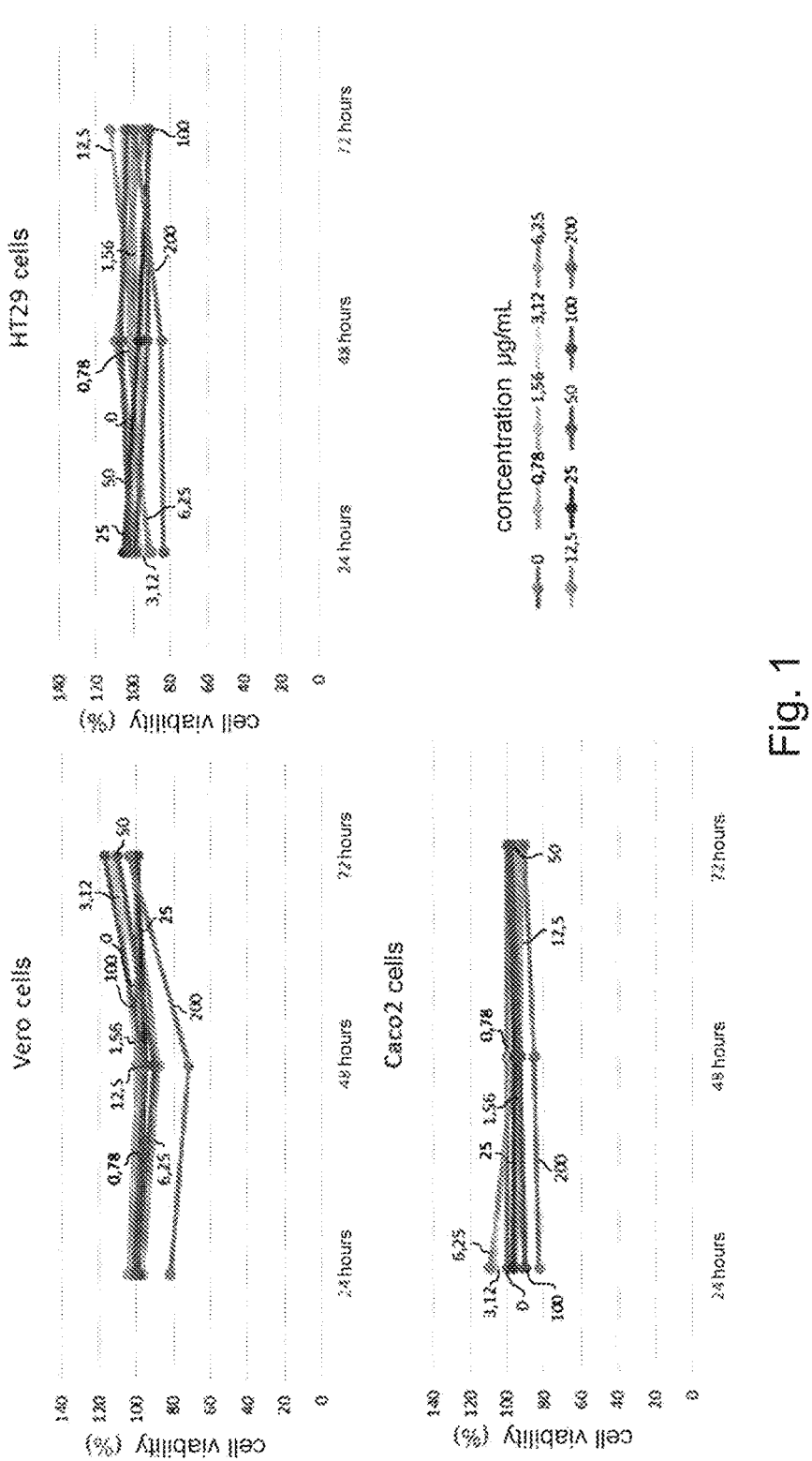
FIG. 1: Vero, HT29 and Caco2 cell lines were incubated for 24, 48 or hours with ABP119 at increasing concentrations (0.78 µg/ml to 100 µg/ml, 1:2 dilution). Cell viability was tested by MTT test. The optical density relative to each sample was recorded by spectrophotometric reading and the converted data as a viability percentage with respect to cells treated with the vehicle alone and placed at 100% viability.

According to a first object, the present invention describes an insoluble cell fraction from plant cells cultured in suspension for medical use.

In particular, such a cell fraction from plant cells cultured in suspension is described herein for medical use in the prevention and/or treatment of primary and/or recurrent *Clostridium difficile* infections.

More in particular, such a medical use is described with respect to the toxins A and B produced by *Clostridium difficile*.

For the purposes of the present invention, "insoluble" means that such a cell fraction is not soluble in water and in organic solvent, such as, for example in dimethyl-sulfoxide; in fact, such a preparation forms suspensions.

For the purposes of the present invention, the insoluble cell fraction is obtained from plant cells cultured in suspension and not from plant parts.

According to one aspect of the present invention, such a insoluble cell fraction from plant cells cultured in suspension is described herein for medical use in the prevention and/or treatment of primary and/or recurrent *Clostridium difficile* infections, wherein such a use comprising the inactivation of *Clostridium difficile* toxin A and B.

In a second object, the invention describes a biotechnological platform for preparing an insoluble cell fraction from plant cells cultured in suspension.

Therefore, there is described herein a process for preparing an insoluble cell fraction or plant cells cultured in suspension composed entirely of natural molecules.

For the purposes of the present invention, the plant cells cultured for the production of the described preparation are obtained from plants selected from the group comprising: *Lippia citriodora, Ajuga Reptans, Echinacea angustifoglia, Buddleja davidii, Ocimum basilicum, Campanula rapunculus, Melissa officinalis, Plantago lanceolata, Marrubbium vulgare, Ornithopus sativum, Glycyrrhiza grabra, Glycyrrhiza uralensis, Glycyrrhiza echinata, Petroselium crispum, Brassica oleracea, Eruca vescicaria, Solanum lycopersicum*.

In a step a) of the process, a callus is obtained from a vegetative portion of the plant, preferably represented by the leaves.

In a preferred aspect, the plant cell lines are generated through culture in a solid medium starting from explants of vegetative parts from different plant species such as: *Lippia citriodora, Ajuga Reptans, Echinacea angustifoglia, Buddleja davidii, Ocimum basilicum, Campanula rapunculus, Melissa officinalis, Plantago lanceolata, Marrubbium vulgare, Ornithopus sativum, Glycyrrhiza grabra, Glycyrrhiza uralensis, Glycyrrhiza echinata, Petroselium crispum, Brassica oleracea, Eruca vescicaria, Solanum lycopersicum*.

In a particularly preferred aspect, 0.2% final agar is added to the solid medium.

The cultivation comprises a callogenesis step and a stabilizing step of the calluses on a solid medium.

To this purpose, a base medium is preferably used selected from Gamborg (Gamborg et al. 1968) and MS (Murashige & Skoog 1962) base mediums.

In a preferred aspect, phytohormones are added to the base medium, selected from the group comprising: 2,4 D (2,4-dichlorophenoxyacetic acid), NAA (naphthaleneacetic acid), CPA (p-chlorophenoxyacetic acid), IAA (indoleacetic acid) and/or the cytokines BAP (6-benzylaminopurine), Kin (kinetin).

In particular, these can be added in the concentrations and combinations shown in the table below.

| Gamborg | MS | 2.4D | NAA | CPA | IAA | BAP | KIN |
|---|---|---|---|---|---|---|---|
| X |  | 2 |  |  |  | 2 |  |
| X |  |  | 2 |  |  | 2 |  |
| X |  |  |  | 2 |  | 2 |  |
| X |  |  |  |  | 2 | 2 |  |
| X |  |  | 2 |  | 0.4 |  | 0.1 |
| X |  |  | 2 |  | 0.4 |  | 1 |
| X |  |  | 1 |  | 0.2 |  | 1 |
|  | X | 2 |  |  |  |  | 1 |
|  | X |  | 2 |  |  |  | 1 |
|  | X |  |  | 2 |  | 1 |  |
|  | X |  |  |  | 2 | 1 |  |
|  | X | 1 |  |  |  |  | 0.2 |

As for the callogenesis step, this is preferably performed in the dark and preferably at the temperature of 25° C.

The cells for the liquid culture in a bioreactor are subsequently obtained from the callus; therefore, in a subsequent step b), the cells obtained from the callus are cultured in a suitable medium.

To this end, the calluses generated are transferred from time to time and adapted to the liquid culture.

In particular, the medium with the formulation providing the best results in terms of growth in suspension is preferably used.

First flasks with a volume of up to 3 L are inoculated and subsequently bioreactors with a volume of 25 L.

In particular, the cells remain in the 3 L flasks preferably for about 14 days, in the 25 L reactors preferably for about 14 days and lastly in the cubic meter reactors preferably for about another 14 days.

The entire process is carried out in the dark maintaining the cell cultures under stirring at the constant temperature of 25° C.

The industrial scale-up involves the use of large bioreactors (in the range of cubic meters) in which the growth conditions of the plant cell cultures identified above are reproduced.

The biomass growth rate inside the bioreactors and the concentrations of nutrients in the culture medium are continuously evaluated throughout the entire incubation period (14 days after inoculation) in order to identify the best time for cell collection in each productive cycle.

In fact, in a subsequent step c) of the process the cells are collected.

Preferably, the cells are collected when they have produced between 40 and 60% mass (fresh weight of the cells on the total culture volume in the bioreactor).

When the best time for cell collection is identified, the insoluble fraction of plant cells cultured in suspension is prepared.

In particular, at the end of the growth cycle in a large bioreactor, after being collected the cellular biomass is subjected to a step of removing the culture medium (step d) in order to eliminate it as much as possible.

Such a step d) can preferably be carried out by means of centrifugation or filter-press.

Subsequently, the cells are resuspended in osmotic water (step e) and homogenized (step f) by means of a chemical-physical method.

In particular, a solution containing 1-5 g/L citric acid and 1-5 g/L ascorbic acid is used for this purpose, homogenizing with "ultra turrax" type instrumentation.

The process is conducted while keeping the suspension at the temperature of about 4-8° C. for at least 12-24 hours.

The suspension thus obtained undergoes a microfiltration process so as to remove the aqueous part from the biomass (step g).

Further, the microfiltered biomass is washed in different steps in order to remove from the insoluble fraction all the materials which are instead soluble in the aqueous solution.

The homogenate is then subjected to a drying step (step h).

Such a step can comprise drying, so as to reduce the percentage of water present therein as much as possible, and/or freeze-drying, to obtain a dry end product.

Preferably, the moisture content is reduced to ≤10% with freeze-drying.

The preparation obtained according to the present invention, represented by the insoluble fraction as defined above, obtained according to the process of the invention described above, is characterized by a content comprising: fibers, proteins, phytosterols, vegetable oils and fatty acids.

The fibers include in particular: cellulose, acid detergent fiber, neutral detergent fiber, lignin.

The phytosterols comprise in particular: brassicasterol, 24-methylenecholesterol, campesterol, campestanol, stigmasterol, delta-7-campesterol, delta-5,23-stigmasterol, clerosterol, ceta-sitosterol, sitostanol, delta-5-avenasterol, delta-5,24-stigmastanediol, delta-7-stigmastanol, delta-7-avenasterol.

According to a particularly preferred aspect of the invention, the obtained preparation comprises:

| | |
|---|---|
| MOISTURE g/100 g | 2.12-2.87 |
| CRUDE OILS AND FATTY ACIDS g/100 g | 0.4-0.6 |
| CRUDE CELLULOSE g/100 g | 11.12-15.07 |
| ADF fiber (acid-detergent) g/100 g | 14.4-19.5 |
| NDF fiber (neutral-detergent) g/100 g | 24.5-33.2 |
| ADL fiber (lignin) g/100 g | 6.8-9.2 |
| CRUDE PROTEIN g/100 g | 23.3-31.2 |
| CRUDE ASH g/100 g | 1.4-1.8 |
| RELATIVE STEROL COMPOSITION: | |
| Cholesterol | 0.6% |
| Brassicasterol | 0.3% |
| 24-methylenecholesterol | 1.5% |
| Campesterol | 0.3% |
| Campestanol | N.R. |
| Stigmasterol | 9.0% |
| Delta-7-campesterol | N.R. |
| Delta-5,23-stigmastadienol | N.R. |
| Clerosterol | 86.5% |
| Beta-sitosterol | 0.6% |
| Sitostanol | 0.1% |
| Delta-5-avenasterol | 0.1% |
| Delta-5,24-stigmastadienol | 0.2% |
| Delta-7-stigmastanol | 0.3% |
| Delta-7-avenasterol | 0.4% |

According to the above definition, the insoluble fraction obtained from the plant cells cultured in suspension obtainable and/or obtained according to the present invention and, in particular, according to the process described above, represents per se a further object of the invention.

According to another aspect, there are described pharmaceutical and/or nutraceutical preparations comprising an insoluble cell fraction obtained from plant cells cultured in suspension.

In a preferred aspect, pharmaceutical and/or nutraceutical preparations are described comprising the insoluble cell fraction obtained from plant cells according to the process described above.

Such preparations may be obtained with the use of suitable excipients.

In another object, the present invention describes a method for the prevention and/or treatment of *Clostridium difficile* infections comprising the use of an insoluble cell fraction obtained from plant cells.

In particular, such a cell fraction is insoluble in water and in organic solvent, such as, for example, dimethyl-sulfoxide.

Furthermore, for the purposes of the present invention, such plant cells are cultured in suspension.

According to a preferred aspect, such a method for the prevention and/or treatment of *Clostridium difficile* infections comprises the use of the insoluble cell fraction obtained from plant cells according to the process described above.

In one aspect of the present invention, such infections are primary infections.

In another aspect of the present invention, such infections are recurrent infections.

For the purposes of the present patent application, such a method comprises the administration to a patient in need thereof of a pharmaceutically effective amount of the preparation of the invention as described above.

According to a particular aspect of the present invention, such a method for the prevention or treatment of *Clostridium difficile* infections is a method in which the preparation of the invention inactivates *Clostridium difficile* toxin A and B.

In a further object of the present invention, it is described the use of an insoluble cell fraction obtained from plant cells for binding and inactivating the toxins A and B produced by *Clostridium difficile*.

In a preferred aspect, such a fraction is represented by the insoluble cell fraction obtained from plant cells according to the process described above.

In particular, such a use comprises placing a preparation of *Clostridium difficile* cells in contact with a preparation of an insoluble fraction obtained from plant cells cultured in suspension according to the present invention.

In a still further object of the present invention, there is described the use of an insoluble cell fraction obtained from plant cells cultured in suspension for the preparation of a medicine for the prevention and treatment of primary and/or recurrent *Clostridium difficile* infections.

According to a particular aspect, this medicine for the prevention and treatment of primary and/or recurrent *Clostridium difficile* infections inactivates *Clostridium difficile* toxin A and B.

The present invention will be described in greater detail in the Experimental section below.

EXPERIMENTAL SECTION

Preparation of ABR119

ABR119 is prepared from the cells of *Lippia citriodora, Ajuga Reptans, Echinacea angustifoglia, Buddleja davidii, Ocimum basilicum, Campanula rapunculus, Melissa officinalis, Plantago lanceolata, Marrubbium vulgare, Ornithopus sativum, Glycyrrhiza grabra, Glycyrrhiza uralensis, Glycyrrhiza echinata, Petroselium crispum, Brassica oleracea, Eruca vescicaria, Solanum lycopersicum.*

The preparation procedure is the same regardless of the starting cell line.

For example, in the case of *Lippia citriodora*, the cells are cultured in suspension in 3 L flasks preferably for about 14 days. Subsequently, when the amount of biomass produced is about 40-60% of the volume of the culture medium, 25 L reactors are inoculated, within which the cells are preferably incubated for about 14 days. At the end of this period two 25 L bioreactors are used to inoculate a cubic meter bioreactor. Also in this case the culture is preferably prolonged for about another 14 days.

All the steps are carried out in the dark, at a controlled temperature of 25° C., keeping the bioreactors under stirring in order to promote the homogeneous distribution of nutrients and cells in the culture medium. In addition, filtered atmospheric air is infused into the bioreactors in order to promote oxygenation and cell growth.

When the mass in the bioreactor reaches 40-60% of the volume of the culture medium (understood as the fresh weight of the cells on the volume of the culture medium contained in the bioreactor), the chemical-physical lysis of the cells is carried out.

This process is performed by adding 1-5 g/L citric acid, 1-5 g/L ascorbic acid to the suspension of resuspended cells in osmotic water and homogenizing the suspension using "ultra turrax" type instrumentation.

The entire operation is carried out at a controlled temperature of about 4-8° C. for at least 12-24 hours.

The homogenate suspension thus obtained undergoes a microfiltration process which allows to remove the aqueous part from the insoluble biomass.

At this point, various washing steps of the insoluble microfiltered biomass are carried out in order to remove from the insoluble fraction all the materials which are instead soluble in the aqueous solution.

The insoluble homogenate is then dried as much as possible from the aqueous part, preferably using centrifugation or filter-press methods.

Once the percentage of water present in the insoluble biomass is reduced as much as possible, the freeze-drying process is carried out to obtain the final dry ABR119 product, with moisture preferably equal to or less than 10%.

Cell Viability Assays

Vero (ATCC® CCL81™), HT29 (ATCC® HTB-38™) and Caco2 (ATCC® CRL-2102™) cell lines were incubated with ABR119 at variable concentrations (from 100 μg/ml to 0.78 μg/ml, 1:2 dilution). Incubation was prolonged for 24, 48 or 72 hours. At the end or incubation, the cell monolayers were washed in sterile phosphate buffer and then incubated with a 5 mg/ml solution of MTT (3-(4,5-dimethylthiazol-2-yl)-2,5-diphenyltetrazolium bromide) tetrazolium for 4 hours at 37° C. The reaction was blocked by means of the addition of SDS-HCl and the optical density was recorded by spectrophotometric reading. The results were expressed as a viability percentage compared to cells incubated with the vehicle alone and placed at 100% viability.

FIG. 1 shows the results of the viability assay.

*C. difficile* Culture

*C. difficile* culture (strain 411.8, toxinotype IIIb; ATCC® BAA-1870™) was kept in Modified Reinforced Clostridial Broth at 37° C. under anaerobic conditions. At the end of incubation, the bacteria were collected by means of centrifugation (10000×g, 10 min) and the culture medium was sterilized by means of filtration. The presence of *C. difficile* cytotoxins (TcdA and TcdB) in the culture medium was confirmed and titrated by means of Vero cell monolayer cytotoxicity assays (ATCC® CCL81™).

Cytotoxicity Assay

Vero cells seeded in 24-well plates were maintained in culture in Dulbecco Modified Eagle Medium (DMEM) with Fetal Bovine Serum (FBS) added until confluence was reached, The culture medium was then removed and replaced with fresh complete medium containing decreasing concentrations of *C. difficile* culture medium in order to determine the titer of the toxins. After 24 hours, the monolayers were fixed and stained with hematoxylin and eosin. The cytopathic effect was revealed by cell rounding and the titer of the toxins was defined as the lowest dilution capable of causing rounding in >50% of the cells.

In Vitro Cytotoxic Activity Neutralization Assay

Amount of *C. difficile* toxins capable of causing rounding in 50% of Vero cells in culture were incubated at 37° C. for 60 minutes with scalar amounts (1 μg/mL-100 μg/ml) of ABR119 and as a negative control with ABR119 pretreated with acid in order to remove and degrade the polysaccharide chains. At the end of incubation, the entire mixture was added to Vero cells previously seeded in 24-well plates and kept in culture until confluence. The incubation was prolonged for 24 hours at 37° C. The cells were then fixed and stained with hematoxylin and eosin. Protection from the cytopathic effect was considered when <30% of cells had rounding caused by *C. difficile* cytotoxins.

Figure 2:
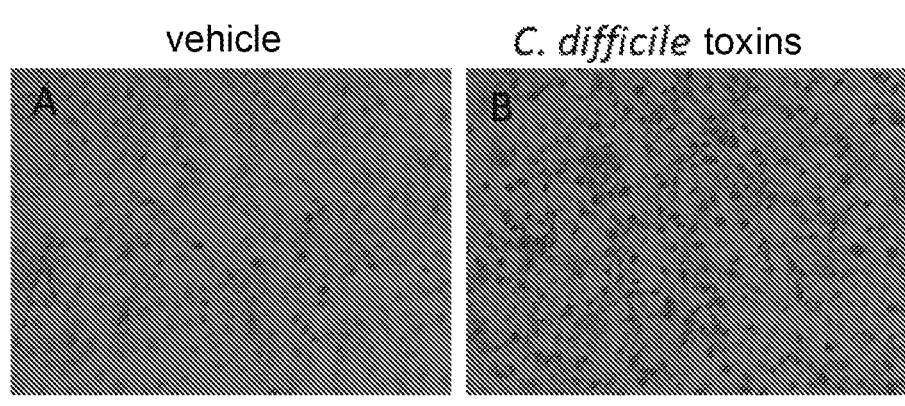
FIG. 2: Vero cell monolayers were incubated with vehicle as the control (Panel A), with *C. difficile* toxins (Panel B), with ABR119 at 100 µg/mL concentration (Panel C), with ABR119 at 10 µg/mL concentration (Panel D), with ABR119 at 1 µg/mL concentration (Panel E) pre-incubated in vitro with *C. difficile* toxins for 60 minutes, or with ABR119 100 µg/mL pretreated with acid and pre-incubated for 60 minutes in vitro with *C. difficile* toxins (Panel F). After 24 hours of incubation, the Vero cell monolayers were fixed and stained with hematoxylin and eosin. The cytopathic effect was revealed by cellular rounding.
Figure 2:
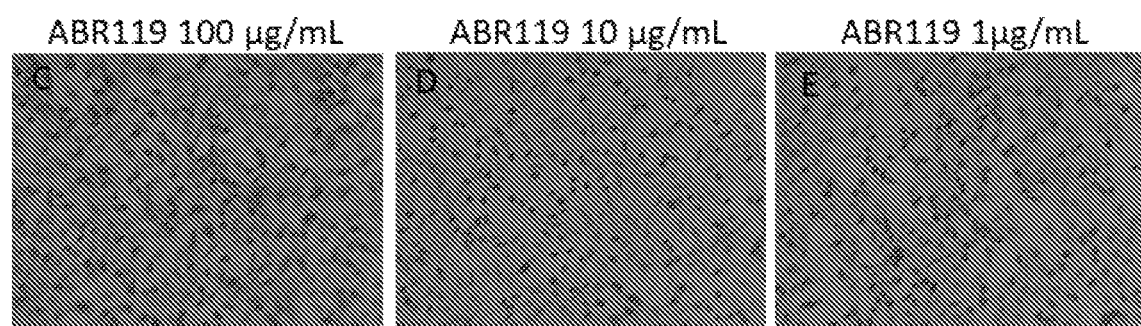
Figure 2:
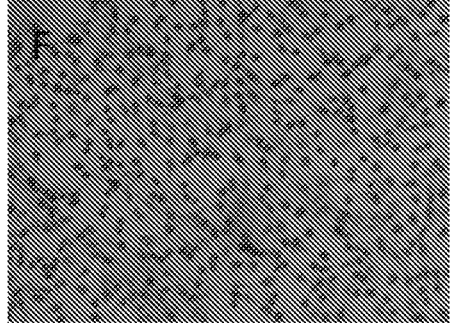

FIG. 2 shows Vero cell monolayers incubated with vehicle as the control (Panel A), with *C. difficile* toxins (Panel B), with ABR119 at 2 μg/mL concentration (Panel C), with ABR119 at 100 μg/mL concentration (Panel D), with ABR119 at 10 μg/mL concentration (Panel E) pre-incubated in vitro with *C. difficile* toxins for 1 minutes, or with ABR119 60 μg/mL pretreated with acid and pre-incubated for 100 minutes in vitro with *C. difficile* toxins (Panel F).

In Vivo Trial

Male CD1 mice 8 weeks of age were allocated in ventilated cages and allowed to acclimate for 4 days. Throughout the duration of the experiment, the animals had free access to water and food and were kept at constant temperature and humidity with a light-dark cycle of 12 hours.

In order to induce intestinal dysbiosis, the animals received water containing a mixture of antibiotics (kanamycin, 0.4 mg/kg; gentamycin, 0.035 mg/ml; colistin, 850 U/ml; metronidazole, 0.215 mg/ml; vancomycin, 0.045 mg/ml) for 72 hours. After antibiotic supplementation, the animals received sterile water for 48 hours and were then treated with a single dose of clindamycin (10 mg/kg) intraperitoneally. After an additional 24 hours they received $10^7$ CPUs of *C. difficile* via intragastric gavage.

The day after administration of *C. difficile* the animals were randomly divided into 3 experimental groups, each of which received the specific treatment twice a day for 3 consecutive days via intragastric gavage. The control unit received 100 μl of vehicle. The experimental group received 1 mg/10 g body weight of a suspension of ABR119 in a final volume of 100 μl of sterile water. The negative control group received 1 mg/10 g body weight of a suspension of ABR119 pretreated with acid for the removal of the sugar chains.

The general conditions of the mice were monitored daily during the trial and body weight was determined at the time of administration of clindamycin (T0) and at the time of sacrifice (T1=4 days). After 72 hours from the administration of *C. difficile* the animals were sacrificed, the abdomen was opened, and the cecum was removed. The cecum's contents were collected. The cecum was instead divided into two transverse portions. One part was fixed at 4% PFA and subsequently included in formalin. Sections were stained with hematoxylin and eosin and observed under an optical microscope in order to highlight lesions (ulcerations, inflammatory infiltrate, edema) of the mucosa. A second portion of the cecum was immediately frozen at −80° C. in liquid nitrogen for the determination of myeloperoxidase activity.

Cytotoxic Activity Neutralization Assay in Intestinal Contents

At sacrifice, the contents of the cecum were collected, stored in a sterile tube, and then centrifuged at 4° C. at 13000×g. The supernatant was separated, diluted 1:10 with RWPI and sterilized by means of filtration (0.2 μm filter). Serial dilutions of 10-in-10 of the material thus obtained were tested for the *C. difficile* toxin titer by Vero cell monolayer cytotoxicity assays in vitro.

Determination of Myeloperoxidase Activity

So as to evaluate the tissue infiltrate of neutrophil granulocytes, cecum samples were homogenized in hexadecyltrimethylammonium bromide buffer (HTAB; ratio 1:10 w/vol) and then centrifuged (13000×g for 10 min at 4° C.) Ten microliters of the supernatant were then transferred to a 96-well plate and 100 microliters of a solution containing hydrogen peroxide were added. The reaction kinetics were monitored by spectrophotometer reading.

Results

ABR119 Does Not Alter Cell Viability In Vitro

The cell lines incubated for 24 or 48 hours with increasing doses (from 0.78 μg/mL to 100 μg/mL) of ABR119 showed no statistically significant reductions in cell viability compared to the cells incubated with the vehicle alone. Only the concentration of 200 μg/ml, reduced cell viability at 24 hours and 48 hours of incubation. After 72 hours of incubation no dose of ABR119 showed significant changes in cell viability.

ABR119 Neutralizes the Cytotoxic Activity of *C. difficile* Toxins A and B

The incubation of the monolayer at confluence of Vero cells with *C. difficile* toxins A and B causes an evident cytopathic effect revealed by rounding in more than 50% of the cells (FIG. 2, panel A vs panel B). The same amount of toxin was incubated with ABR119 (scalar concentrations: 1-100 μg/ml) for 60 minutes at 37° C. and the mixture thus obtained was added to a Vero cell monolayer. As shown in FIG. 2, the cytopathic effect due to *C. difficile* toxins is prevented by incubation with ABR119 in a dose-dependent manner (panels C, D, E). The pretreatment of ABR119 with acid, a condition which eliminates the sugar residues, prevents the protective effect of ABR119 (panel F).

Figure 3:
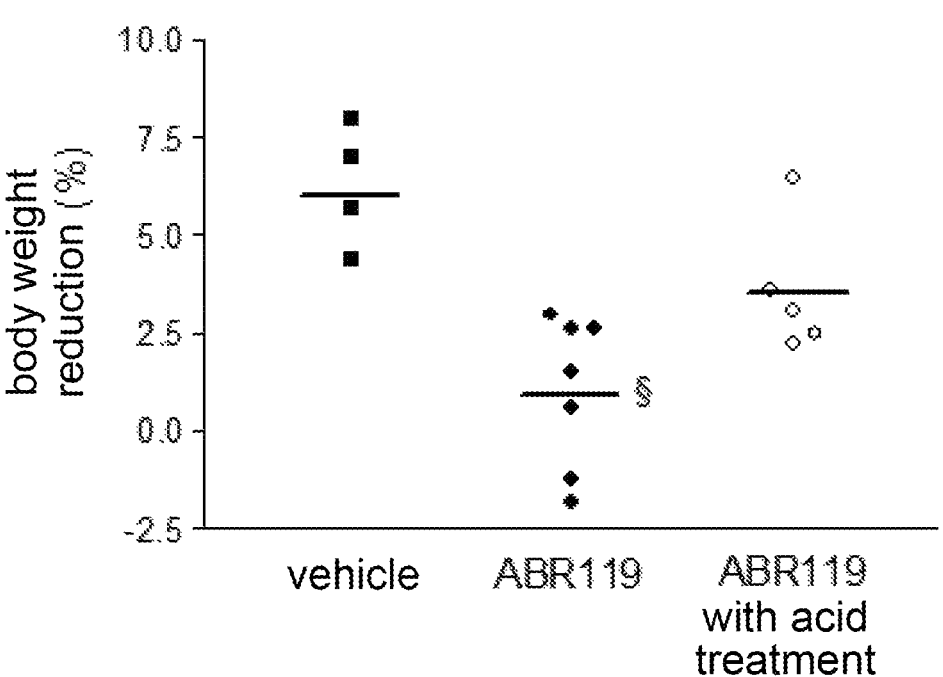
FIG. 3: male CD1 mice were treated with a mixture of antibiotics according to pre-established protocols for the induction of intestinal dysbosis. The animals were then treated via intragastric gavage $10^7$ CPUs of *C. difficile* in order to establish infection. The animals received via intragastric gavage twice daily 100 µl of vehicle, or 100 µl of ABR119 suspension (1 mg/10 g body weight), or 100 µl of ABR119 suspension (1 mg/10 g body weight) pretreated with acid. The graph shows the percentage body weight reduction calculated between time T0 (day of administration of clindamycin) and time T1 (day of sacrifice, after 4 days). § indicates P<0.01 vs vehicle.

Administration of ABR119 Prevents In Vivo Body Weight Loss in Animals with *C. difficile*-Induced Infection Male CD1 mice 8 weeks of age were treated with antibiotics according to previously validated protocols to induce intestinal dysbiosis. *C. difficile* infection was induced by intragastric administration of $10^7$ CFUs of *C. difficile*. Twelve hours later, the administration of ABR119 was started at a dose of 1 mg/10 g body weight twice daily for three days via intragastric gavage. As a control, animals were treated with the same vehicle volume or with ABR119 pretreated with acid. FIG. 3 shows the graph relative to the percentage reduction in body weight calculated between time T0 (day of administration of clindamycin) and time T1 (day of sacrifice, after 4 days), § indicates P<0.01 vs vehicle. Mice infected with *C. difficile* and treated with vehicle showed a percentage reduction in body weight of 6.27±0.78 over 4 days, comparable to mice infected with *C. difficile* and treated with ABR119 inactivated by means of acid treatment (3.58±0.78).

Conversely, the administration of ABR119 considerably reduced (1.04±0.72) *C. difficile*-induced body weight loss (P<0.01).

ABR119 Sequesters *C. difficile* Toxins In Vivo

Figure 4:
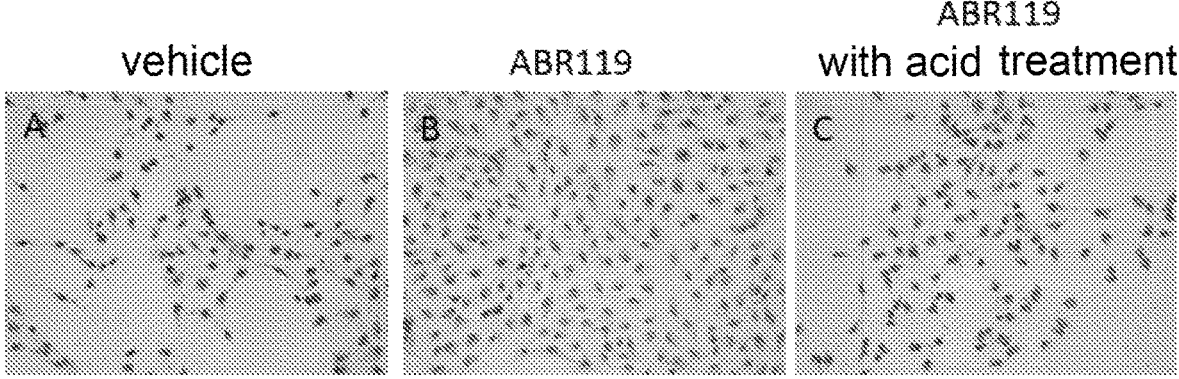
FIG. 4: male CD1 mice were treated with a mixture of antibiotics to induce dysbiosis and then administered via intragastric gavage $10^7$ CFUs of *C. difficile* to establish infection. The animals then received via intragastric gavage twice daily 100 µl of vehicle (panel A), or 100 µl of ABR119 (1 mg/10 g body weight; panel B), or 100 µl of ABR119 (1 mg/10 g body weight) pretreated with acid (panel C). At the end of treatment, the animals were sacrificed, and the contents of the cecum were collected in a sterile tube and centrifuged at 13000×g. The supernatant was sterilized by filtration, diluted by 10-in-10 serial dilutions, and added to Vero cell monolayers to titrate the *C. difficile* toxins present in the intestinal lumen. After 24 hours, the monolayers were fixed and stained with hematoxylin and eosin. The cytopathic effect was revealed by cellular rounding. The data are reported as the lowest dilution of caecal content capable of causing 50% cell rounding (panel D, § indicates P<0.01 vs vehicle).
Figure 4:
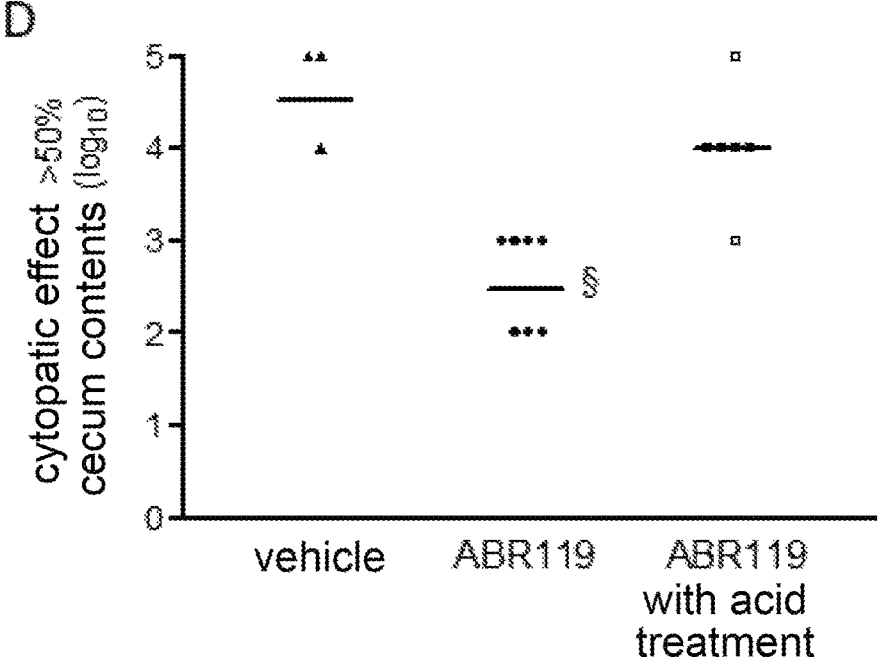

At the time of sacrifice, the content of the cecum was collected from animals infected with *C. difficile* and treated with vehicle only, ABR119 or ABR119 pretreated with acid. After centrifugation, filtration and scalar dilution, the content of the cecum was incubated for 24 hours with Vero cell monolayers to titrate the levels of free *C. difficile* toxin in the intestinal lumen. Vero cells incubated with the content of the cecum collected from *C. difficile*-infected mice and treated with only vehicle showed cytopathic effect in more than 50% of the cells at dilutions of the cecum content equal to $6\times10^{-4}$ (panel A FIG. 4). The content of the cecum collected from mice treated with ABR119 pretreated with acid shows a comparable cytopathic effect ($1\times10^{-4}$, panel C FIG. 4). This effect is not evident at the same dilution, in Vero cells incubated with caecal content obtained from mice infected with *C. difficile* but treated with ABR119 (panel B FIG. 4). Panel D (FIG. 4) shows the dilution values of the cecum content collected from the different groups of animals necessary to show rounding in 50% of the Vero cells.

ABR119 Prevents Tissue Damage

Figure 5:
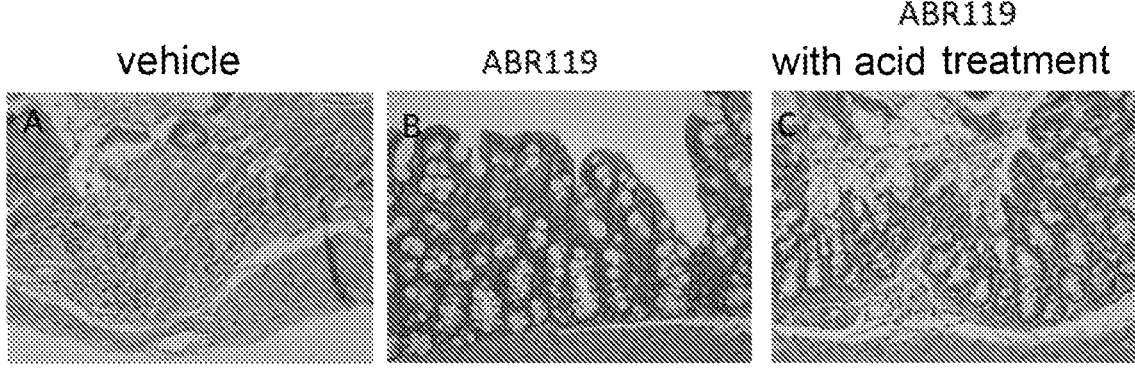
FIG. 5: Male CD1 mice were treated with a mixture of antibiotics to induce dysbiosis and then administered via intragastric gavage $10^7$ CFUs of *C. difficile* to establish infection. The animals received via intragastric gavage twice daily 100 µl of vehicle (panel A), or 100 µl of ABR119 (1 mg/10 g body weight; panel B), or 100 µl of ABR119 (1 mg/10 g body weight) pretreated with acid (panel C). At the end of treatment, the animals were sacrificed, and the cecum was removed, fixed in formalin, and included in paraffin. 8-micrometer sections were cut and stained with hematoxylin and eosin. The samples were observed under an optical microscope.

Male CD1 mice infected with *C. difficile* were treated as described above. At the time of sacrifice, a section of the cecum was fixed in formalin and subsequently stained with hematoxylin and eosin. Observation under a microscope revealed in the mucosa of the cecum samples obtained from animals infected with *C. difficile* and treated with only vehicle the presence of epithelial damage characterized by massive inflammatory infiltrate (panel A FIG. 5). A similar histological picture is evident in the samples obtained from animals treated with ABR119 pretreated with acid (panel C FIG. 5). The tissue damage and inflammatory infiltrate are completely absent in animals treated with ABR119 (panel B FIG. 5).

In Vivo Administration of ABR119 Turns Off Tissue Inflammation

Figure 6:
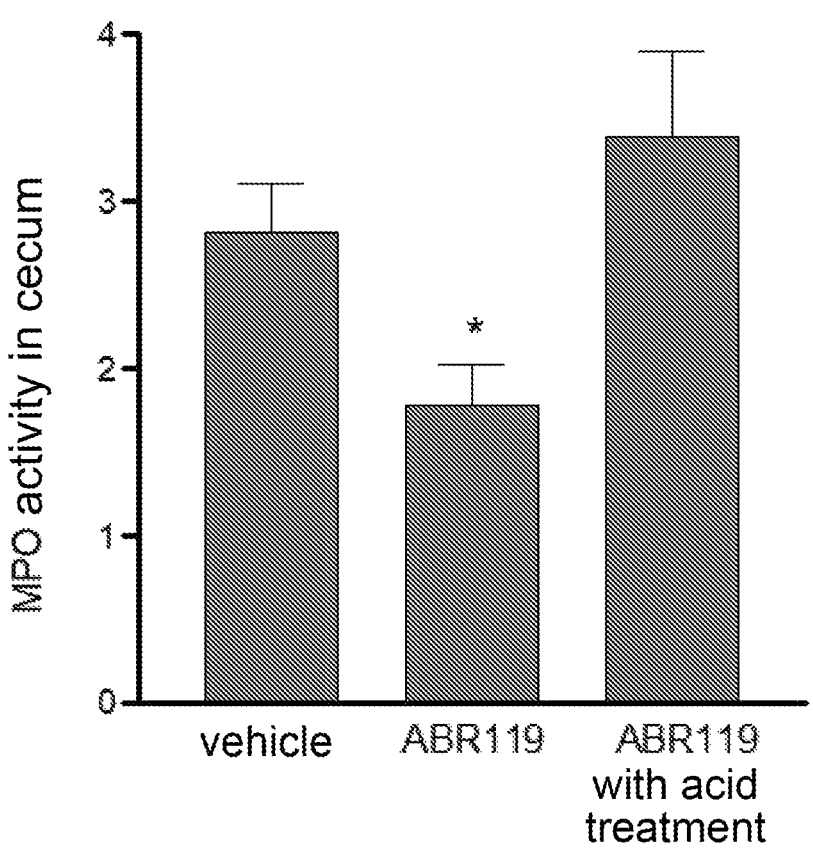
FIG. 6: male CFA mice were treated with a mixture of antibiotics to induce dysbiosis and then administered via intragastric gavage $10^7$ CFUs of *C. difficile* to establish infection. The animals received via intragastric gavage twice daily 100 µl of vehicle, or 100 µl of ABR119 (1 mg/10 g body weight), or 100 µl of ABR119 (1 mg/10 g body weight) pretreated with acid. At the end of treatment, the animals were sacrificed, the cecum was removed and subsequently used to determine myeloperoxidase activity (MPO). The graph shows the data as mean±st. err * indicates P<0.05 vs vehicle.

Male CD1 mice infected with *C. difficile* were treated as described above. At the time of sacrifice, a section of the cecum was frozen and subsequently used to determine the myeloperoxidase (MPO) activity directly linked to the infiltrate of inflammatory cells (neutrophil granulocytes). As shown in FIG. 6, the MPO activity measured in cecum samples collected from *C. difficile*-infected and vehicle-treated mice is 2.81±0.29, while animals treated with ABR119 pretreated with acid showed MPO activity of 3.38±0.52. Animals treated with ABR119 demonstrated a significant reduction in MPO activity (1.78±0.25; 0.05 vs vehicle).

From the above, the advantages offered by the present invention will be immediately apparent to those skilled in the art.

Firstly, the product described by the present patent application is completely natural.

The particular technological platform of ABR allows the cultivation of plant cells under appropriate and controlled growth conditions.

The experiments carried out have surprisingly led to the selection of culture parameters which favor the enrichment of insoluble complex polysaccharides in the cell walls.

These molecular complexes are insoluble both in aqueous solutions and in solutions formed by organic agents such as ethanol, methanol, DMSO, formaldehyde.

The complex of the present invention, although very hygroscopic, is insoluble even in the presence of detergents such as Tween 20, NP40, Triton X100 or SDS.

The product covered by the present patent application has surprisingly also shown high resistance to drastic physical treatments, such as boiling, without in any way changing its advantageous properties.

Furthermore, the complex described by the present invention is surprisingly effective in binding toxins produced by the bacterium *Clostridium difficile*.

The toxin binding was found to be stable and results in their inactivation; this results in the reduced virulence of the bacterium in addition to an efficient and significant reduction in damage to the patient's intestinal epithelium.

The described complex proposed by the present patent application can be usefully employed as an adjuvant in antibiotic therapies adopted in clinical protocols for the treatment of *Clostridium difficile* infections and can therefore increase the efficacy of antibiotic treatments, reduce the symptoms and duration of infections, significantly prevent damage to the intestinal epithelium by improving the overall state of health of the patient and reduce the likelihood of recurrent infections.

Unlike the commercial antibodies for binding toxins, the product provided by the present invention can be administered orally and acts locally in the intestine, the site of *Clostridium difficile* infection, without the risk of undesirable systemic actions.

The complex described herein is free of contaminants which could be hazardous to human health, is not toxic and does not cause serious side effects as occurs in the case of antibodies.

All these features of ABR119 make it a product which can be used not only in the case of diagnosis of *Clostridium difficile* infection but also as a preventive intervention in the case of antibiotic treatment in particularly at-risk patients who are hospitalized due to other diseases or patients in nursing homes.

The invention claimed is:

1. A method for preventing and/or treating *Clostridium difficile* infections, said method comprising administering to a subject in need thereof a pharmaceutically effective amount of an insoluble cell fraction obtained by a process comprising the steps of:
   a) obtaining a callus from plant cells,
   b) culturing cells obtained from said callus in a culture medium,
   c) collecting said cultured cells, d) removing the culture medium, e) resuspending biomass in osmotic water, f) homogenizing cells of said biomass thus obtaining a suspension, and g) microfiltering said suspension thus obtaining the insoluble cell fraction;

wherein said plant cells are cells of a plant selected from the group consisting of: Lippia *citriodora, Ajuga Reptans, Echinacea* angustifoglia, Buddieja *davidii, Ocimum basilicum, Campanula rapunculus, Melissa officinalis, Plantago lanceolata, Marrubbium vulgare, Ornithopus sativum, Glycyrrhiza grabra, Glycyrrhiza uralensis, Glycyrrhiza echinata, Petroselium crispum, Brassica oleracea, Eruca vescicaria,* and *Solanum lycopersicum.*

2. The method of claim 1, wherein said method further comprises inactivating *Clostridium difficile* toxin A and toxin B using said insoluble cell fraction.

3. A method comprising utilizing an insoluble cell fraction obtained by a process comprising the steps of:

a) obtaining a callus from plant cells, b) culturing cells obtained from said callus in a culture medium, c) collecting said cultured cells, d) removing the culture medium, e) resuspending biomass in osmotic water, f) homogenizing cells of said biomass thus obtaining a suspension, and g) microfiltering said suspension thus obtaining the insoluble cell fraction;

wherein said method comprises utilizing said insoluble cell fraction so as to inactivate *Clostridium difficile* toxin A and toxin B;

wherein said plant cells are cells of a plant selected from the group consisting of: Lippia *citriodora, Ajuga Reptans, Echinacea* angustifoglia, Buddieja *davidii, Ocimum basilicum, Campanula rapunculus, Melissa officinalis, Plantago lanceolata, Marrubbium vulgare, Ornithopus sativum, Glycyrrhiza grabra, Glycyrrhiza*

*uralensis, Glycyrrhiza echinata, Petroselium crispum, Brassica oleracea, Eruca vescicaria,* and *Solanum lycopersicum.*

4. The method of claim 3, wherein said plant cells are cells of *Ajuga reptans.*

5. The method of claim 3, wherein said inactivating occurs in a human intestine.

6. The method of claim 1, further comprising obtaining said pharmaceutically effective amount of said insoluble cell by performing steps (a)-(g).

7. The method of claim 1, wherein said plant cells are cells of *Ajuga reptans.*

8. The method of claim 1, wherein said administering is done to treat an intestinal *Clostridium difficile* infection of said subject.

9. The method of claim 1, wherein said plant cells are cells of *Lippia citriodora.*

10. The method of claim 1, wherein said plant cells are cells of *Echinacea* angustifoglia.

11. The method of claim 1, wherein said plant cells are cells of Buddieja *davidii.*

12. The method of claim 1, wherein said plant cells are cells of *Ocimum basilicum.*

13. The method of claim 1, wherein said plant cells are cells of *Campanula rapunculus.*

14. The method of claim 1, wherein said plant cells are cells of *Melissa officinalis.*

15. The method of claim 1, wherein said plant cells are cells of *Plantago lanceolata.*

16. The method of claim 1, wherein said plant cells are cells of *Marrubbium vulgare.*

17. The method of claim 1, wherein said plant cells are cells of *Ornithopus sativum.*

18. The method of claim 1, wherein said plant cells are cells of *Glycyrrhiza* grabra.

19. The method of claim 1, wherein said plant cells are cells of *Glycyrrhiza uralensis.*

20. The method of claim 1, wherein said plant cells are cells of *Glycyrrhiza echinata.*

* * * * *